United States Patent [19]
Kalopissis et al.

[11] 3,989,447
[45] Nov. 2, 1976

[54] PROCESS FOR NONPERMANENTLY DYEING HUMAN HAIR WITH INDAMINE INDOANILINE AND INDOPHENOL HAIR DYES

[75] Inventors: Gregoire Kalopissis, Paris; Andrée Bugaut, Boulogne-sur-Seine; Francoise Estradier; Giuliana Ghilardi, Paris; Jean-Francois Grollier, Paris; Pierre Bore, Montfermeil, all of France

[73] Assignee: L'Oreal, Paris, France

[22] Filed: May 27, 1975

[21] Appl. No.: 580,787

Related U.S. Application Data

[63] Continuation of Ser. No. 189,795, Oct. 15, 1971, abandoned.

[30] Foreign Application Priority Data
Oct. 19, 1970 Luxembourg .............................. 61889

[52] U.S. Cl. .......................................... 8/10.1; 8/10; 8/10.2; 8/11; 424/DIG. 2

[51] Int. Cl.$^2$ .......................................... A61K 7/13
[58] Field of Search .................. 8/10, 10.1, 10.2, 11

[56] References Cited
UNITED STATES PATENTS

| | | | |
|---|---|---|---|
| 1,019,576 | 5/1912 | Woffenstein et al. | 8/10.2 |
| 2,960,443 | 11/1960 | Rosmarin | 8/10.2 |
| 3,194,734 | 7/1965 | Seemuller | 8/10.2 |
| 3,698,852 | 10/1972 | Pantzer | 8/10.2 |

Primary Examiner—V. D. Turner
Assistant Examiner—Vera C. Clarke
Attorney, Agent, or Firm—Cushman, Darby & Cushman

[57] ABSTRACT

A process for nonpermanently dyeing human hair comprises applying to the hair a dye composition prepared immediately before application of the same to the hair, the composition comprising an aqueous solution of a solid anhydrous dye selected from the group consisting of indamine, indoaniline and indophenol hair dyes, present in the composition in amounts of 0.0005-2 percent by weight thereof.

13 Claims, No Drawings

PROCESS FOR NONPERMANENTLY DYEING HUMAN HAIR WITH INDAMINE INDOANILINE AND INDOPHENOL HAIR DYES

This is a continuation, of application Ser. No. 189,795 filed Oct. 15, 1971, now abandoned.

This invention relates to a process for nonpermanently dyeing human hair by applying to the hair a hair dye composition which is prepared immediately prior to applying the same to the hair by incorporating in an aqueous carrier a solid anhydrous dye selected from the group consisting of indamine, indoaniline and indophenol hair dyes.

It is known that there are two general modes of dyeing hair which differ from each other according to the nature of the dye employed and the results achieved therewith. These modes are generally known as permanent and nonpermanent dyeing processes. A permanent dyeing process is characterized by the fact that the resulting dyeing exhibits good fastness to washings, resists several shampooings and is achieved, generally, with oxidation dyes, i.e., colorless dyes which develop the desired coloration in situ under the influence of an oxidizing agent. On the other hand, a nonpermanent dyeing process is characterized by the fact that the resulting dyeing does not exhibit as favorable or comparable fastness to washing characteristics as those attainable in a permanent dyeing process although it does offer the advantage of permitting the user to easily change or modify the color of the hair. Generally nonpermanent dyeing processes utilized direct dyes such as azo, anthraquinone and aromatic nitro dyes. As it is known, however, these direct dyes fail to produce colorations having sufficient transparency or glints or at least not to the degree achievable with the use of oxidation dyes, as in a permanent dyeing process. And it is recognized by those in this field that these aesthetic characteristics are highly desirable in any type of hair dyeing, be it permanent or nonpermanent.

It is also known that indoanilines, indamines and indophenols can be used to dye hair. However, up to the present, their extensive use has been curtailed because of their lack of acceptable stability characteristics in solutions. The applicants have now developed a process which permits the use of these dyes for nonpermanent dyeing of hair, which process consists in using these dyes, not in the form of a prepackaged dyeing solution, as is usually the case with conventional dyeing processes, but by incorporating these dyes in an aqueous solution immediately prior to applying the same to the hair.

Representative indamines, indoanilines and indophenols usefully employed in the process of the present invention are those having the formula,

including tautomers thereof, wherein Ar₁ and Ar₂, each independently, represent an aromatic hydrocarbon or heterocyclic nucleus, each optionally substituted with a member selected from the group consisting of amino, hydroxy, lower alkoxy, lower alkyl, acylamino and halogen such as chlorine and bromine, Y represents a member selected from the group consisting of hydroxy and

wherein $R_1$ and $R_2$ each independently represent a member selected from the group consisting of hydrogen, lower alkyl, hydroxy lower alkyl and amino lower alkyl with the amine function being optionally substituted or acylated, and X represents a member selected from the group consisting of oxygen, imine and iminium groups, or salts of these compounds.

In this context, lower alkyl and lower alkoxy mean those having 1–4 carbon atoms. Further, the nomenclature adopted for these dyeing compounds corresponds to a numbering of the Ar₁ and Ar₂ nuclei which, in the case of phenyl nuclei, is as follows:

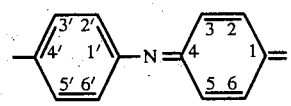

Representative indamines that can be used in the present invention are hydrochloride of N-[(4'-dimethylamino) phenyl] 3-amino 6-methyl benzoquinonediimine, the monoacetate of N-[(4'-amino 2'-methoxy 5'-methyl) phenyl] 2-aza 3-amino benzoquinonediimine, the double chloride of zinc and N-[4'-(ethyl, β-acetylaminoethyl) -amino phenyl] 3-amino 6-methoxy benzoquinonediimine, the monoacetate of N-[(4'-amino 2'-methoxy 5'-methyl) phenyl] 3-amino 6-methyl benzoquinonediimine and the double chloride of zinc and N-[4'-(ethyl, β-acetylaminoethyl) -amino phenyl] 3-hydroxy benzoquinoneimine N',N'-diethyliminium.

Representative indoanilines that can be used in the present invention are, for instance, N-[(4'-dimethylamino) phenyl] 2,6-dimethyl benzoquinoneimine, N-[(4'-dimethylamino) phenyl] 2,5-dimethyl benzoquinoneimine, N-[4'-amino 2'-methoxy 3',5'-dimethyl) phenyl] 2,6-dimethyl benzoquinoneimine, N-[(4'-amino 2'-methoxy 3',5'-dimethyl) phenyl] 2,5-dimethyl benzoquinoneimine, N-[4'-dimethylamino) phenyl] 3-amino 6-methyl benzoquinoneimine, N-[(4'-amino 2'-methoxy) phenyl] 3-amino 6-methyl benzoquinoneimine, N-[4'-amino 2'-methoxy 5'-methyl) phenyl] 3-acetylamino 6-methyl benzoquinoneimine, N-[(4'-hydroxy) phenyl] 3-amino 6-methoxy benzoquinonediimine, N-[(4'-hydroxy) phenyl] 3-amino benzoquinonediimine and N-[(4'-amino 3'-chloro) phenyl] 3-amino 2,6-dimethyl benzoquinoneimine.

Representative indophenols that can be used in the present invention include N-[(4'-hydroxy) phenyl] 2,6-dimethyl benzoquinoneimine, N-[(4'-hydroxy) phenyl] 2,5-dimethyl benzoquinoneimine, N-[(4'-hydroxy) phenyl] 3-amino 6-methyl benzoquinoneimine and N-[(4'-hydroxy 3',5'-dimethyl) phenyl] 2,6-dimethyl benzoquinoneimine.

Other indophenols, indamines and indoanilines suitably employed are those disclosed in commonly assigned U.S. patent applications Ser. No. 45,564, filed June 11, 1970, now abandoned; Ser. No. 49,905, filed June 25, 1970, now abandoned; Ser. No. 52,739, filed July 6, 1970, now U.S. Pat. No. 3,677,690; Ser. No. 97,395, filed Dec. 11, 1970, now abandoned; Ser. No.

100,433, filed Dec. 21, 1970, now abandoned, and Ser. No. 161,887, now U.S. Pat. No. 3,758,268, (CIP of 52,739,) filed July 12, 1971.

According to the present invention, the indamines, indoanilines and indophenols can be used in powder or tablet form. For purposes of definition the term "powder" is used to designate powders, per se, i.e., discrete particulate matter as well as powders in shaped forms, such as tablets. It is advantageous that the powders used be as finely divided as possible, so that they dissolve rapidly and easily. These powders are kept from all moisture until the time of application.

The powders used in the process according to the invention can also include other direct dyes, in particular, azo dyes, anthraquinone dyes or aromatic nitro derivatives, or again lyophilisate oxidation products with oxidation bases or coupler-oxidation base mixtures. These lyophilisates are described in commonly assigned U.S. patent application Ser. No. 120,353, filed Mar. 2, 1971, now abandoned.

The powders used in the process according to the invention can also include cosmetic resins, optical bluings or other additives usually used in capillary cosmetic such as thickeners, wetting agents, surfactants, swelling agents, penetrating agents or sun filters.

The indamines, indoanilines or indophenols can also be present in these powders simply crystallized or microencapsulated. They can also be in coated form.

The above dye or dyes are put into solution at the time of application by mixing the powder with a suitably selected amount of an aqueous solution of appropriate composition.

The aqueous solution used can be simply made up of water to which, if necessary, there is added a suitable amount of acid or base so as to regulate the pH of the final composition to a value between 4 and 10. The aqueous solution or carrier can also contain one or more low molecular weight alcohols such as ethanol or isopropanol, dyeing adjuvants such as butylglycol or benzyl alcohol, surfactants, sun filters such as benzylidene camphor, optical bluings, antioxidizing agents such as butylhydroxyanisol and/or additives usually used in capillary cosmetics, such as thickeners, wetting agents, swelling agents, penetrating agents or perfumes.

In a particular embodiment of the process according to the invention, the aqueous solution used contains hydrogen peroxide in a proportion of 1 to 6% by weight and the final solution, prepared immediately before application to the hair, constitutes a bleaching dyeing composition.

In another embodiment of the process according to the present invention, the powder and/or aqueous solution can contain one or more cosmetic resins such as polyvinylpyrrolidone having a molecular weight ranging between 40,000–360,000, preferably about 40,000, a copolymer of crotonic acid-vinyl acetate 90%:10% having a molecular weight of 40,000–200,000, preferably 50,000 and a viscosity of 7–9 cp in a 5% solution in tetrachloroethane, a copolymer of vinylpyrrolidone-vinyl acetate (M.W. = 40,000–160,000), 70%:30% to 30%:70%, the preferred proportion being 60%:40% having a viscosity of 3.3–4 cp in 5% solution in ethanol or maleic anhydride-butylvinyl ether copolymers in such a proportion that this resin constitutes 1 to 3% by weight of the final composition. In this case, said final composition, prepared immediately before application to the hair, constitutes a colored hair-setting lotion.

As has already been said, the pH of the hair dye composition, prepared immediately before application to the hair by mixing said powder with said aqueous solution, is usually between 4 and 10, this pH being obtained by adding to the aqueous solution a base or acid in suitable amount. However, it is possible to utilize with some dyes a pH as low as 2.5.

The concentration of indamines, indoanilines or indophenols in the composition that is ready to use can be extremely slight because of the great dyeing power of these compositions. This concentration generally varies between 0.0005% and 2% by weight of the total.

Dyeing of the hair according to the process of the present invention is performed preferably by simply applying the composition which is obtained by mixing the dye powder with the aqueous solution just before application of the same to the hair followed by putting up the hair on rollers or curlers and/or drying the hair, without previously rinsing or washing the hair. However, in another embodiment of this process, it is possible to wash or rinse the hair before putting it up on rollers or curlers or drying it.

The process according to the invention offers the advantage of making it possible to achieve nonpermanent dyeings exhibiting glints and transparency essentially comparable to that achieved in a permanent dyeing process using oxidization dyes, and without having the disadvantage inherent in using oxidation dyes, which are generally applied in the presence of hydrogen peroxide.

The process according to the invention further makes it possible to use temporary unstable dispersions of indamines, indoanilines and indophenols of a higher concentration than the upper solubility limit of these dyes. This fact, plus the ability of using extremely slight concentrations of these dyes, offers the additional advantage of making it possible to obtain a particularly broad range of shades.

The following examples are intended to show the present invention, it being understood that these examples do not present any limiting character.

EXAMPLE 1

A hair setting lotion and dyeing composition is prepared by mixing immediately before application 0.025 g of a powder $P_1$ and 25 cc of a solution $S_1$, having the following compositions:

Powder $P_1$:
Hydrochloride of N-[(4'-dimethylamino) phenyl]3-amino 6-methyl benzoquinonediimine      2.5 g
Polyvinylpyrrolidone (M.W. 40,000), q.s.p.      100 g
Solution $S_1$:
Vinylpyrrolidone-vinyl acetate copolymer 70/30 (M.W. 40,000 to 50,000)      2 g
Triethanolamine, q.s.p.      pH 9
Water, q.s.p.      100 cc When applied to natural black hair and after drying, this composition imparts to the hair a very bright bluish glint.

EXAMPLE 2

A hair setting lotion and dyeing composition is prepared by mixing at the time of use 0.1 g of a powder $P_2$ and 25 cc of a solution $S_2$, having the following compositions:

| Powder P₂: | |
|---|---|
| Double chloride of zinc and N-[4'-(ethyl, β-acetylaminoethyl)-amino] phenyl] 3-hydroxy benzoquinoneimine N',N'-diethyliminium | 5.0 g |
| N-[(4'-hydroxy) phenyl] 2,6-dimethyl benzoquinoneimine | 1.0 g |
| Polyvinylpyrrolidone (as in Example 1), q.s.p. | 100 g |
| Solution S₂: | |
| Crotonic acid-vinyl acetate copolymer, 90/10, M.W. 50,000 to 55,000 | 2.0 g |
| Ethyl alcohol | 50 g |
| Triethanolamine, q.s.p. | pH 7 |
| Water, q.s.p. | 100 cc |

When applied to natural blond hair and after drying this composition imparts to the hair a very aesthetic ash-gray coloration.

EXAMPLE 3

A hair setting lotion and dyeing composition is prepared by mixing at the time of use 0.1 g of a powder P₃ and 25 cc of a solution S₃ defined below:

| Powder P₃: | |
|---|---|
| Double chloride of zinc and of N-[4'-ethyl, β-acetylaminoethyl)-amino phenyl]3-hydroxy benzoquinoneimine N',N'-diethyliminium | 1.0 g |
| N-[(4'-amino, 2'-methoxy, 3',5'-dimethyl) phenyl] 2,6-dimethyl benzoquinoneimine | 2.0 g |
| Vinylpyrrolidone-vinyl acetate copolymer 70/30 (as in Example 1), q.s.p. | 100 g |
| Solution S₃: | |
| Vinylpyrrolidone-vinyl acetate copolymer (as above) | 2.0 g |
| N-acetylethanolamine | 0.15 g |
| Water, q.s.p. | 100 cc |
| Citric acid, q.s.p. | pH 5 |

When applied to naturally white hair, and after drying, this composition imparts to the hair a very bright silver ash-gray glint. Further, the hair thus treated is easy to set.

EXAMPLE 4

A hair setting lotion and dyeing composition is prepared by mixing at the time of use 0.1 g of a powder P₄ and 25 cc of a solution S₄ defined below:

| Powder P₄: | |
|---|---|
| Monoacetate of N-[(4'-amino 2'-methoxy 5'-methyl) phenyl] 2-aza 3-amino benzoquinonediimine | 1.0 g |
| Hydrochloride of N-[(4'-dimethylamino) phenyl] 3-amino 6-methyl benzoquinonediimine | 5.0 g |
| Vinylpyrrolidone-vinyl acetate copolymer 70/30 (as in Example 1), q.s.p. | 100 g |
| Solution S₄: | |
| Vinylpyrrolidone-vinyl acetate copolymer 70/30 (as above) | 2 g |
| Butyl Cellosolve | 0.2 g |
| Ethanol | 50 g |
| N-acetylethanolamine | 0.15 g |
| Benzylidene camphor | 0.2 g |
| Butylhydroxyanisole | 0.15 g |
| Water, q.s.p. | 100 g |

When applied to naturally white hair, and after drying, this composition imparts to the hair a very bright silvery glint.

EXAMPLE 5

A hair setting lotion and dyeing composition is prepared by mixing at the time of use 0.1 g of a powder P₅ and 25 cc of a solution S₅ defined below:

| Powder P₅: | |
|---|---|
| N-[(4'-amino 2'-methoxy 5'-methyl) phenyl] 3-acetylamino 6-methyl benzoquinoneimine | 2.0 g |
| N-(4'-hydroxy phenyl) 3-amino 6-methyl benzoquinoneimine | 2.0 g |
| N-[(4'-hydroxy) phenyl] 2,6-dimethyl benzoquinoneimine | 1.5 g |
| Vinylpyrrolidone-vinyl acetate copolymer 70/30 (As in Example 1), q.s.p. | 100 g |
| Solution S₅: | |
| Crotonic acid-vinyl acetate copolymer 90/10 (as in Example 2) | 2.0 g |
| Ethanol | 50 g |
| Benzylidene camphor | 0.2 g |
| Triethanolamine, q.s.p. | pH 6.5 |
| Water, q.s.p. | 100 g |

When applied to hair previously bleached and tinted in a very light blond, and after drying, this composition imparts to the hair a bright and particularly aesthetic ash-gray glint.

EXAMPLE 6

A hair setting lotion and dyeing composition is prepared by mixing at the time of use 0.1 g of a powder P₆ and 25 cc of a solution S₆ defined below:

| Powder P₆: | |
|---|---|
| N-[(4'-hydroxy) phenyl] 2,5-dimethyl benzoquinoneimine | 0.7 g |
| N-[(4'-dimethylamino) phenyl] 2,6-dimethyl benzoquinoneimine | 0.3 g |
| Vinyl pyrrolidone-vinyl acetate copolymer (as in Example 1) | 100 g |
| Solution S₆: | |
| Crotonic acid-vinyl acetate copolymer (as in Example 2) | 2.0 g |
| Ethanol | 55 g |
| 20 volume hydrogen peroxide | 5 g |
| Orthophosphoric acid, q.s.p. | pH 3 |
| Water, q.s.p. | 100 g |

When applied to natural light brown hair, and after putting the hair up on curlers and drying, the hair is slightly lighter and in addition has a very bright and very transparent pearly glint.

EXAMPLE 7

A hair setting lotion and dyeing composition is prepared by mixing at the time of use 0.1 g of a powder P₇ and 25 cc of a solution S₇ defined below:

| Powder P₇: | |
|---|---|
| N-[(4'-amino 2'-methoxy) phenyl] 3-amino 6-methyl benzoquinoneimine | 0.3 g |
| N-[(4'-amino 2'-methoxy 3',5'-dimethyl) phenyl] 2,5-dimethyl benzoquinoneimine | 0.6 g |
| Vinylpyrrolidone-vinyl acetate copolymer 70/30 (as in Example 1), q.s.p. | 100 g |

-continued

| Solution S₇: | |
|---|---|
| Vinylpyrrolidone-vinyl acetate copolymer 70/30 (as above) | 2.0 g |
| Ethanol | 50 g |
| Uvitex SWN concentrated (Fluorescent Brightening Agent of the Color Index(CI 141 S 615) sold by CIBA | 0.060 g |
| Triethanolamine, q.s.p. | pH 7 |
| Water, q.s.p. | 100 g |

When applied to light blond hair presenting freshly bleached locks, and after drying, a particularly aesthetic and bright pearly ash-gray glint is observed.

EXAMPLE 8

A hair setting lotion and dyeing composition is prepared by mixing at the time of use 25 cc of solution $S_2$ described in Example 2 and 0.1 g of a powder $P_8$ described below:

| Powder P₈: | |
|---|---|
| N-[(4'-dimethylamino) phenyl] 3-amino 6-methyl benzoquinoneimine | 8.0 g |
| N-[(4'-dimethylamino) phenyl] 2,5-dimethyl benzoquinoneimine | 1.0 g |
| Vinylpyrrolidone-vinyl acetate copolymer (as in Example 1), q.s.p. | 100 g |

When applied to hair previously tinted a light brown, and after drying, this composition imparts to the hair a very bright ash-gray glint.

EXAMPLE 9

A hair setting lotion and dyeing composition is prepared by mixing at the time of use 0.15 g of a solid $P_9$, in tablet form, and 25 cc of a solution $S_9$ defined below:

| Tablet P₉: | |
|---|---|
| N-[(4'-hydroxy) phenyl] 3-amino 6-methyl benzoquinonediimine | 8.0 g |
| Double chloride of zinc and N-[4'-(ethyl-β-acetylaminoethyl) -amino] phenyl] 3-amino 6-methoxy benzoquinonediimine | 4.0 g |
| Vinylpyrrolidone-vinyl acetate copolymer 70/30 (as in Example 1), q.s.p. | 100 g |
| Solution S₉: | |
| Crotonic acid-vinyl acetate copolymer (as in Example 2) | 2.0 g |
| Ethanol | 50 g |
| Benzylidene camphor | 0.2 g |
| Butylhydroxyanisole | 0.1 g |
| Triethanolamine, q.s.p. | pH 7 |
| Water, q.s.p. | 100 cc |

When applied to hair tinted chestnut, and after drying, this composition imparts to the hair a very bright purplish dark auburn glint and the thus treated hair is easy to set.

EXAMPLE 10

A hair setting lotion and dyeing composition is prepared by mixing at the time of use 25 cc of solution $S_5$ described in Example 5 and 0.1 g of a powder $P_{10}$ defined below:

| Powder P₁₀: | |
|---|---|
| Monoacetate of N-[(4'amino 2'-methoxy 5'-methyl) phenyl] 3-amino 6-methyl benzoquinonediimine | 3 g |

-continued

| Powder P₁₀: | |
|---|---|
| N-[(4'-hydroxy 3',5'-dimethyl) phenyl] 2,6-dimethyl benzoquinoneimine | 10 g |
| Vinylpyrrolidone-vinyl acetate copolymer (as in Example 1), q.s.p. | 100 g |

When applied to hair previously bleached and tinted blond, and after drying, this composition imparts to the hair a very bright beige pearly gray shade.

EXAMPLE 11

A hair setting lotion and dyeing composition is prepared by mixing at the time of use 25 cc of solution $S_5$ described in Example 5 and 0.015 g of a powder $P_{11}$ defined above.

| Powder P₁₁: | |
|---|---|
| N-[(4'-hydroxy) phenyl] 2,5-dimethyl benzoquinoneimine | 8.0 g |
| Bromide of 4-methyl 8-di-β-hydroxyethyl-amino - morpholino [2, 3-b] phenoxazonium | 20 g |

When applied to hair that has been bleached and tinted a dark chestnut, and after drying, a very bright bluish ash-gray glint is observed. The hair is light and easy to do.

EXAMPLE 12

A rinsing and dyeing composition is prepared by mixing at the time of use 0.2 g of a powder $P_{12}$ and 30 cc of a solution $S_{12}$ defined below:

| Powder P₁₂: | |
|---|---|
| Colored lyophilisate prepared according to Example 3 of U.S. application Serial No. 120,353 filed March 2, 1971 | 99.8 g |
| N-[(4'-hydroxy) phenyl] 3-amino 6-methyl benzoquinonediimine | 0.2 g |
| Solution S₁₂: | |
| Hydroxyethyl cellulose sold as "Natrosol 250 L" by Hercules Powder | 0.4 g |
| Vinyl pyrrolidone-vinyl acetate copolymer (as in Example 1) | 0.3 g |
| Ethanol | 10 g |
| Citric acid, q.s.p. | pH 4.5 |
| Water, q.s.p. | 100 g |

When applied to freshly bleached hair, which is then put up on curlers and, after drying, the hair exhibits a light pearly blond shade.

EXAMPLE 13

A rinsing and dyeing composition is prepared by mixing at the time of use 0.05 g of the powder described in Example 1 of Ser. No. 120,353 and 30 cc of a solution $S_{13}$ defined below:

Solution $S_{13}$:

| | |
|---|---|
| Hydroxyethyl cellulose sold as "Natrosol 250 L" by Hercules Powder | 0.4 g |
| Citric acid, q.s.p. | pH 4 |
| Water, q.s.p. | 100 cc |

When applied to natural dark brown hair having some white hair, and after drying, a camouflage of the white hair is observed in a very bright, slightly ash-gray shade.

EXAMPLE 14

A hair setting lotion and dyeing composition is prepared by mixing at the time of use 25 cc of solution $S_4$ described in Example 4 of Ser. No. 120,353 and 0.1 g of a powder $P_{14}$ defined below:

Powder $P_{14}$:

| | |
|---|---|
| N-[(4'-dimethylamino) phenyl] 2,6-dimethyl benzoquinoneimine | 10.0 g |
| Nitroparaphenylenediamine | 5.0 g |
| Vinylpyrrolidone-vinyl acetate copolymer 70/30 (as in Example 1), q.s.p. | 100 g |

When applied to hair tinted auburn, and after drying, this composition imparts to the hair a very bright, slightly purplish copper glint.

EXAMPLE 15

A hair setting lotion and dyeing composition is prepared by mixing at the time of use 25 cc of solution $S_2$ described in Example 2 of Ser. No. 120,353 and 0.1 g of a powder $P_{15}$ defined below:

Powder $P_{15}$:

| | |
|---|---|
| N-[(4'-hydroxy) phenyl] 3-amino 6-methyl benzoquinoneimine | 10 g |
| 1-methylamino γ-aminopropylamino-4 anthraquinone | 5.0 g |
| Vinylpyrrolidone-vinyl acetate copolymer 70/30 (as in Example 1), q.s.p. | 100 g |

When applied to hair previously bleached and tinted a light chestnut, and after drying, a very bright pearly ash-gray glint is observed.

EXAMPLE 16

A dyeing composition is prepared by mixing 50 cc of solution $S_{12}$ described in Example 12 of Ser. No. 120,353 and 0.00045 g of a powder $P_{16}$ defined below:

Powder $P_{16}$:

| | |
|---|---|
| N[(4'-hydroxy) phenyl] 3-amino 6-methyl benzoquinoneimine | 98 g |
| N-[(4'-amino 2'-methoxy 3',5'-dimethyl) phenyl] 2,6-dimethyl benzoquinoneimine | 2 g |

When applied to light freshly bleached light hair and after setting and drying, the hair exhibits a very light golden pearly bond shade, very transparent and very bright.

EXAMPLE 17

A dyeing composition is prepared by mixing at the time of use 0.45 g of powder $P_{12}$ described in Example 12 and 25 cc of solution $S_4$ described in Example 4.

This solution is applied as a hair-setting lotion to hair bleached and tinted chestnut. After setting and drying, the hair, brilliant and easy to do, exhibits a particularly regular reddish brown shade.

EXAMPLE 18

A rinsing and dyeing composition is prepared by mixing at the time of use 0.02 g of powder $P_4$ described in Example 4 of Ser. No. 120,353 and 25 cc of a solution $S_{18}$ defined below:

Solution $S_{18}$:

| | |
|---|---|
| Hydroxyethyl cellulose sold as "Natrosol 250 L" by Hercules Powder | 0.3 g |
| "Ethomeen C" (condensation product of 5 moles of ethylene oxide on coconut amine) sold by Armour | 0.1 g |
| Citric acid, q.s.p. | pH 3.5 |
| Water, q.s.p. | 100 cc |

When applied in a rinse to hair bleached and tinted a very light blond, and after drying, the hair exhibits a very light ash-gray blond shade, extremely luminous and transparent.

EXAMPLE 19

A hair dyeing composition is prepared by mixing at the time of use 0.4 g of a powder $P_{19}$ and 50 g of a gelified solution $S_{19}$ defined below:

Powder $P_{19}$:
Colored lyophilisate prepared according to Example 3 of application Serial No. 120,353

Solution $S_{19}$:

| | |
|---|---|
| Crotonic acid-vinyl acetate copolymer (as in Example 2) | 2 g |
| Ethyl alcohol | 20 g |
| Carbopol 940 (carboxyvinyl polymer, carboxypolymethylene) sold by B.F. Goodrich | 0.5 g |
| Triethanolamine | 0.8 g |
| Water, q.s.p. | 100 g |

This gel is applied to dark blond hair comprising 10% white hair. After drying, the hair exhibits a uniform golden brown shade.

EXAMPLE 20

A hair setting lotion and dyeing composition is prepared by mixing at the time of use 0.10 g of powder $P_{20}$ defined below and 25 cc of solution $S_2$ described in Example 2.

Powder $P_{20}$:

| | |
|---|---|
| N-[(4'-hydroxy) phenyl] 2,6-dimethyl benzoquinoneimine | 9.0 g |
| N-[(4'-hydroxy) phenyl] 3-amino 6-methyl benzoquinoneimine | 4.0 g |
| Butylhydroxyanisole | 25 g |
| Optical bluing sold under the trade name "Uvitex SWN" by CIBA (CI 141 S 615) | 15 g |
| Vinylpyrrolidone-vinyl acetate copolymer 70/30 (as in Example 1) q.s.p. | 100 g |

When applied to bleached hair tinted golden chestnut, and after drying, the hair exhibits a very luminous copper shade.

EXAMPLE 21

A dyeing composition is prepared by mixing at the time of use 0.0003 g of a powder $P_{21}$ and 25 cc of a solution $S_{21}$ defined below:

| Powder $P_{21}$: | |
|---|---|
| Hydrochloride of N-[(4'-dimethylamino) phenyl] 3-amino 6-methyl benzoquinone-diimine | 20 g |
| N-[(4'-hydroxy) phenyl] 3-amino 6-methyl benzoquinoneimine | 80 g |
| Solution $S_{21}$: | |
| Carboxymethylcellulose, sold under the trade name "Cellulose gum 7 M" by Hercules Powder | 0.2 g |
| Triethanolamine, q.s.p. | pH 9 |
| Water, q.s.p. | 100 cc |

When applied to very light blond hair, and after drying, the hair exhibits a very bright emerald green glint.

EXAMPLE 22

A colored hair-setting lotion is prepared by mixing at the time of use 0.038 g of a powder $P_{22}$ defined below and 25 cc of solution $S_2$ described in Example 2.

| Powder $P_{22}$: | |
|---|---|
| Metal-bearing dye "Acid Red 184" of the Color Index (CI 15685) | 94.8 g |
| Hydrochloride of N-[(4'-dimethylamino) phenyl] 3-amino 6-methyl benzoquinone-diimine | 5.2 g |

When applied to blond hair, this setting lotion imparts to the hair a particularly aesthetic pearly blond shade.

EXAMPLE 23

A colored hair-setting lotion is prepared by mixing at the time of use 0.12 g of a powder $P_{23}$ and 25 cc of a solution $S_{23}$ defined below.

| Powder $P_{23}$: | |
|---|---|
| N-[(4'-amino 2'-methoxy 3',5'-dimethyl) phenyl] 2,6-dimethyl benzoquinoneimine | 1 g |
| Vinylpyrrolidone-vinyl acetate copolymer 70/30 (as in Example 1), q.s.p. | 100 g |
| Solution $S_{23}$: | |
| Ethanol | 96 g |
| Water, q.s.p. | 100 g |

This solution is applied to graying hair. After drying, the hair presents a particularly brilliant and aesthetic silvery glint.

EXAMPLE 24

A hair setting lotion dyeing composition is prepared by mixing at the time of use 25 cc of solution $S_2$ described in Example 2 and 0.1 g of a powder $P_{24}$ defined below.

| Powder $P_{24}$: | |
|---|---|
| N-[(4'-hydroxy) phenyl] 2,6-dimethyl benzoquinoneimine | 2 g |
| N-[(4'-dimethylamino) phenyl] 2,5-dimethyl benzoquinoneimine | 0.5 g |
| N-[(4'-dimethylamino) phenyl] 2,6-dimethyl benzoquinoneimine | 0.3 g |
| Vinylpyrrolidone-vinyl acetate copolymer 70/30 (as in Example 1), q.s.p. | 100 g |

When applied to hair bleached and tinted blond, and after drying, the composition imparts to the hair a very luminous pearly glint.

EXAMPLE 25

A dyeing composition is prepared by mixing at the time of use 25 cc of solution $S_5$ described in Example 5 and 0.1 g of powder $P_{25}$ defined below.

| Powder $P_{25}$: | |
|---|---|
| N-[(4'-hydroxy) phenyl] 2,6-dimethyl benzoquinoneimine | 1 g |
| N-[(4'-hydroxy) phenyl] 3-amino benzoquinoneimine | 2 g |
| N-[(4'-dimethylamino) phenyl] 2,6-dimethyl benzoquinoneimine | 0.5 g |
| Vinylpyrrolidone-vinyl acetate copolymer 70/30 (as in Example 1), q.s.p. | 100 g |

This composition is applied to hair bleached and tinted chestnut. After drying, the hair exhibits a particularly aesthetic dark auburn glint.

EXAMPLE 26

A hair-setting lotion and dyeing composition is prepared by mixing at the time of use 25 cc of solution $S_2$ described in Example 2 and 0.075 g of a powder $P_{26}$ defined below.

| Powder $P_{26}$: | |
|---|---|
| N-[(4'-hydroxy) phenyl] 2,6-dimethyl benzoquinoneimine | 2 g |
| Hydrochloride of N-[(4'-dimethylamino) phenyl] 3-amino 6-methyl benzoquinone-diimine | 0.1 g |

When applied to hair that has been bleached and tinted a very light blond, this hair-setting lotion imparts thereto a very pretty pearly golden glint.

EXAMPLE 27

A hair-setting lotion and dyeing composition is prepared by mixing at the time of use 25 cc of solution $S_4$ described in Example 4 and 0.12 g of powder $P_{27}$ defined below.

| Powder $P_{27}$: | |
|---|---|
| N-[(4'-amino 3'-chloro) phenyl] 3-amino 2,6-dimethylbenzoquinoneimine | 2 g |
| Vinylpyrrolidone-vinyl acetate copolymer 70/30 (as in Example 1), q.s.p. | 100 g |

This composition when applied to hair bleached and tinted blond, imparts thereto a pretty, very luminous pearly glint.

EXAMPLE 28

A dyeing composition is prepared by mixing at the time of use 50 cc of a solution $S_{28}$ and 0.03 g of a powder $P_{28}$ defined below.

| | |
|---|---|
| Powder $P_{28}$: | |
| N-[(4'-hydroxy) phenyl] 2,6-dimethyl benzoquinoneimine | 67 g |
| N-[(4'-dimethylamino) phenyl] 2,5-dimethyl benzoquinoneimine | 33 g |
| Solution $S_{28}$: | |
| Butyl Cellosolve | 8 g |
| Propylene glycol | 8 g |
| Condensation product of nonylphenol with 4 moles of ethylene oxide, sold under the name "Remcopal 334" by Gerland Co. | 22 g |
| Condensation product of nonylphenol with 9 moles of ethylene oxide, sold under the name "Remcopal 349" by Gerland Co. | 22 g |
| Water, q.s.p. | 100 g |

By adding 50 g of water to 50 g of the solution thus prepared, a gel is obtained which is applied to bleached hair. After 30 minutes, the hair is rinsed and dried. A very light beige shade is obtained.

EXAMPLE 29

A hair-setting lotion is prepared by mixing immediately before application on the hair, 0.100 g of a powder $P_{30}$ and 25 cc of a solution $S_{29}$ having the following compositions:

| | |
|---|---|
| Powder $P_{29}$: | |
| N-[(4'-amino 3',5'-dimethyl) phenyl] 3-acetylamino 6-methyl benzoquinoneimine | 3 g |
| N-[(4'-amino 2'-methoxy 3',5'-dimethyl) phenyl] 2,5-dimethyl benzoquinoneimine | 1 g |
| N-[(4'-hydroxy) phenyl] 3-amino 6-methyl benzoquinoneimine | 1.5 g |
| Polyvinylpyrrolidone (as in Example 1), q.s.p. | 100 g |
| Solution $S_{29}$: | |
| Crotonic acid-vinyl acetate copolymer 90/10 (as in Example 2) | 2.0 g |
| Ethanol | 50 cc |
| Triethanolamine, q.s.p. | pH 7 |
| Water, q.s.p. | 100 cc |

When applied to natural hair presenting a great percentage of white hair, and after drying, this composition imparts to the hair a very luminous and particularly aesthetic silvery ash-gray glint.

EXAMPLE 30

A hair-setting lotion is prepared by mixing immediately before use 0.100 g of a powder $P_{30}$ and 25 cc of a solution $S_{30}$ having the following compositions:

| | |
|---|---|
| Powder $P_{30}$: | |
| N-[(4'-hydroxy) phenyl] 2,6-dimethyl benzoquinoneimine | 22 g |
| N-[(4'-hydroxy) phenyl] 3-acetylamino 2,6-dimethyl benzoquinoneimine | 11 g |
| N-[(4'-hydroxy) phenyl] 3-amino 6-methyl benzoquinoneimine | 11 g |
| N-[4'-(ethyl, carbamylmethyl) -amino 2'-methyl] phenyl] 3-amino 6-methyl benzoquinoneimine | 0.5 g |
| Polyvinylpyrrolidone (as in Example 1), q.s.p. | 100 g |
| Solution $S_{30}$: | |
| Vinylpyrrolidone-vinyl acetate copolymer 70/30 (as in Example 2) | 2 g |
| Ethanol | 50 cc |
| N-acetylethanolamine | 0.15 g |
| Benzylidene camphor | 0.2 g |
| Butylhydroxyanisole | 0.15 g |
| Triethanolamine, q.s.p. | pH 7 |
| Water, q.s.p. | 100 cc |

When applied to hair tinted dark auburn chestnut, and after drying, the hair exhibits a very aesthetic, strong coppery auburn glint.

EXAMPLE 31

A hair-setting lotion is prepared by mixing immediately before application to the hair 0.100 g of a powder $P_{31}$ and 25 cc of a solution $S_{31}$ of the following composition:

| | |
|---|---|
| Powder $P_{31}$: | |
| N-[(4'-hydroxy 2',6'-dimethyl) phenyl] 2,6-dimethyl benzoquinoneimine | 5 g |
| Polyvinylpyrrolidone (as in Example 1), q.s.p. | 100 g |
| Solution $S_{31}$: | |
| Crotonic acid-vinyl acetate copolymer (as in Example 2) | 2.0 g |
| Ethyl alcohol | 40 cc |
| Triethanolamine, q.s.p. | pH 8 |
| Water, q.s.p. | 100 cc |

When applied to hair freshly bleached to a very light blond, and after drying, the hair exhibits a particularly aesthetic, slightly pearly very light blond shade.

EXAMPLE 32

A hair-setting lotion is prepared by mixing, immediately before application, 0.100 g of a powder $P_{32}$ and 25 cc of a solution $S_{32}$ of the following compositions:

| | |
|---|---|
| Powder $P_{32}$: | |
| N-[(4'-amino 3',5'-dimethyl) phenyl] 2,6-dimethyl benzoquinoneimine | 4 g |
| N-[(4'-hydroxy) phenyl] 3-amino 6-methyl benzoquinoneimine | 1 g |
| Polyvinylpyrrolidone (as in Example 1), q.s.p. | 100 g |
| Solution $S_{32}$: | |
| Crotonic acid-vinyl acetate copolymer (as in Example 2) | 2.0 g |
| Ethanol | 50 cc |
| Benzylidene camphor | 0.2 g |
| Butylhydroxyanisole | 0.1 g |
| Triethanolamine, q.s.p. | pH 6.5 |
| Water, q.s.p. | 100 cc |

When applied to hair tinted blond, and after drying, the hair exhibits a very luminous and very aesthetic ash-gray blond shade.

EXAMPLE 33

A hair-setting lotion is prepared by mixing, immediately before application, 0.130 g of a powder $P_{33}$ and 25 cc of a solution $S_{33}$ having the following compositions:

| | |
|---|---|
| Powder $P_{33}$: | |
| N-[(4'-hydroxy) phenyl] 3-amino 6-methyl benzoquinonediimine | 3.8 g |
| N-[(4'-dimethylamino) phenyl] 3-acetylamino 6-methyl benzoquinoneimine | 1.5 g |
| Polyvinylpyrrolidone (as in Example 1), q.s.p. | 100 g |
| Solution $S_{33}$: | |
| Crotonic acid-vinyl acetate copolymer 90/10 (as in Example 2) | 2 g |
| Ethanol | 50 g |
| Benzylidene camphor | 0.2 g |
| Triethanolamine, q.s.p. | pH 7 |

-continued

| | |
|---|---|
| Water, q.s.p. | 100 cc |

When applied to hair tinted chestnut, and after drying, the hair exhibits a very aesthetic purplish glint.

EXAMPLE 34

A hair-setting lotion is prepared by mixing, immediately before application, 0.120 g of a powder $P_{34}$ and 25 cc of a solution $S_{34}$ having the following compositions:

| | |
|---|---|
| Powder $P_{34}$: | |
| N-[(4'-hydroxy) phenyl] 3-amino 6-methyl benzoquinoneimine | 4.16 g |
| N-[(4'-amino 2',5'-dimethyl) phenyl] 2,6-dimethyl benzoquinoneimine | 0.83 g |
| Polyvinylpyrrolidone (as in Example 1), q.s.p. | 100 g |
| Solution $S_{34}$: | |
| Polyvinylpyrrolidone (as in Example 1) | 1.5 g |
| Ethyl alcohol | 50 cc |
| Butylhydroxyanisole | 0.1 g |
| Triethanolamine, q.s.p. | pH 7 |
| Water, q.s.p. | 100 cc |

When applied to natural blond hair, and after drying, the hair exhibits a slight ash-gray pearly glint.

EXAMPLE 35

A dyeing composition is prepared by mixing before application 0.200 g of a powder $P_{35}$ and 25 cc of a solution $S_{35}$ having the following compositions:

| | |
|---|---|
| Powder $P_{35}$: | |
| N-[(4'-amino) phenyl] 2,6-dimethyl benzoquinoneimine | 5 g |
| Polyvinylpyrrolidone (as in Example 1), q.s.p. | 100 g |
| Solution $S_{35}$: | |
| 20 volume hydrogen peroxide | 5 cc |
| Orthophosphoric acid, q.s.p. | pH 3 |
| Ethyl alcohol | 50 cc |
| Water, q.s.p. | 100 cc |

When applied as a rinse to light naturally chestnut hair, and after drying, the hair is brightened and, in addition, exhibits a very aesthetic pearly glint.

EXAMPLE 36

A hair-setting lotion is prepared by mixing, immediately before application, 0.018 g of a powder $P_{36}$ and 25 cc of a solution $S_{36}$ of the following compositions:

| | |
|---|---|
| Powder $P_{36}$: | |
| N-[(4'-amino 3'-methyl) phenyl] 2,6-dimethyl benzoquinoneimine | 10 g |
| N-[(4'-hydroxy 2',6'-dimethyl) phenyl] 2,6-dimethyl benzoquinoneimine | 5 gg |
| N-[4'-hydroxy) phenyl] 3-acetylamino 2,6-dimethyl benzoquinoneimine | 3 g |
| Solution $S_{36}$: | |
| Crotonic acid-vinyl acetate copolymer 90/10 (as in Example 2) | 2 g |
| Ethyl alcohol | 50 cc |
| Benzylidene camphor | 0.2 g |
| Triethanolamine, q.s.p. | pH 8.5 |
| Water, q.s.p. | 100 cc |

When applied to natural hair comprising 30% white hair, and after drying, the white hair exhibits a bluish ash-gray glint and is particularly camouflaged.

EXAMPLE 37

A hair-setting lotion is prepared by mixing, immediately before application, 0.150 g of a powder $P_{37}$ and 25 cc of a solution $S_{37}$ having the following compositions:

| | |
|---|---|
| Powder $P_{37}$: | |
| N-[(4'-amino 3'-methyl 6'-methoxy) phenyl] 2,6-dimethyl benzoquinoneimine | 3.3 g |
| N-[(4'-amino 3',5'-dimethyl) phenyl] 3-amino 6-methyl benzoquinoneimine | 1.65 g |
| Polyvinylpyrrolidone (as in Example 1), q.s.p. | 100 g |
| Solution $S_{37}$: | |
| Crotonic acid-vinyl acetate copolymer 90/10 (as in Example 2) | 20 g |
| Ethyl alcohol | 50 cc |
| Triethanolamine, q.s.p. | pH 6 |
| Water, q.s.p. | 100 cc |

When applied to hair containing 90% white hair, a very luminous bluish ash-gray shade is obtained.

EXAMPLE 38

A hair-setting lotion is prepared by mixing, immediately before application, 0.100 g of a powder $P_{38}$ and 25 cc of a solution $S_{38}$ of the following compositions:

| | |
|---|---|
| Powder $P_{38}$: | |
| N-[(4'-hydroxy) phenyl] 2,6-dimethyl benzoquinoneimine | 19 g |
| N-[(4'-hydroxy) phenyl] 3-acetylamino 2,6-dimethyl benzoquinoneimine | 8 g |
| N-[(4'-hydroxy) phenyl] 3-amino 6-methyl benzoquinoneimine | 7 g |
| N-[(4'-amino 3',5'-dimethyl) phenyl] 3-acetylamino 6-methyl benzoquinoneimine | 4 g |
| Polyvinylpyrrolidone (as in Example 1) | 63 g |
| Solution $S_{38}$: | |
| Crotonic acid-vinyl acetate copolymer (as in Example 2) | 1.5 g |
| Ethyl alcohol | 50 cc |
| Triethanolamine, q.s.p. | pH 7.5 |
| Water, q.s.p. | 100 cc |

When applied to hair tinted chestnut, and after drying, the hair exhibits a particularly regular and luminous dark auburn chestnut shade.

EXAMPLE 39

A hair-setting lotion is prepared by mixing, immediately before application, 0.100 g of a powder $P_{39}$ and 100 cc of a solution $S_{39}$ of the following compositions:

| | |
|---|---|
| Powder $P_{39}$: | |
| N-[(4'-dimethylamino) phenyl] 3-amino 6-methyl benzoquinoneimine | 8 g |
| N-[4'-hydroxy) phenyl] 2,5-dimethyl benzoquinoneimine | 8 g |
| N-[(2',4'-diamino 5'-methyl) phenyl] 2-chlorobenzoquinoneimine | 12 g |
| Polyvinylpyrrolidone (as in Example 1), q.s.p. | 100 g |
| Solution $S_{39}$: | |
| Crotonic acid-vinyl acetate copolymer (as in Example 2) | 1.5 g |
| Ethyl alcohol | 50 cc |
| Triethanolamine, q.s.p. | pH 7.5 |
| Water, q.s.p. | 100 cc |

When applied to freshly bleached hair, and after drying, the hair exhibits a very uniform and particularly aesthetic beige shade.

EXAMPLE 40

A dyeing composition is prepared by mixing, immediately before application, 0.002 g of a powder $P_{40}$ and 25 cc of a solution $S_{40}$ of the following compositions:

| Powder $P_{40}$: | |
|---|---|
| N-[(4'-hydroxy) phenyl] 2,3-dimethyl benzoquinoneimine | 50 g |
| N-[(4'-(ethyl, β-mesylaminoethyl)-amino 2'-methyl] phenyl] 2,5-dimethyl benzoquinoneimine | 50 g |
| Solution $S_{40}$: | |
| Ethyl alcohol | 30 cc |
| Butyl Cellosolve | 10 cc |
| Triethanolamine, q.s.p. | pH 7 |
| Water, q.s.p. | 100 cc |

When applied as a rinse to light blond hair, and after drying, the hair exhibits a very aesthetic ash-gray light blond shade.

EXAMPLE 41

A hair-setting lotion is prepared by mixing immediately before application 0.025 g of a powder $P_{41}$ and 25 cc of a solution $S_{41}$ having the following compositions:

| Powder $P_{41}$: | |
|---|---|
| N-[[4'-(ethyl, β-mesylaminoethyl) -amino 2'-methyl] phenyl] 2,5-dimethyl benzoquinoneimine | 8 g |
| N-[(4'-amino 2',5'-dimethyl) phenyl] 2,6-dimethyl benzoquinoneimine | 20 g |
| Polyvinylpyrrolidone (as in Example 1), q.s.p. | 100 g |
| Solution $S_{41}$: | |
| Vinylpyrrolidone-vinyl acetate copolymer (as in Example 1) | 2.0 g |
| Ethyl alcohol | 50 cc |
| Ethyl Cellosolve | 5 cc |
| Triethanolamine, q.s.p. | pH 7 |
| Water, q.s.p. | 100 cc |

When applied to hair tinted ash-blond, and after drying, the hair is still more ash-gray, beautiful and brilliant.

EXAMPLE 42

A dyeing composition is prepared by mixing, immediately before application, 25 cc of solution $S_{35}$ described in Example 35 and 0.010 g of a powder $P_{42}$ defined below:

| Powder $P_{42}$: | |
|---|---|
| N-[(4'-hydroxy) phenyl] 2,3-dimethyl benzoquinoneimine | 50 g |
| N-[(4'-hydroxy 2',6'-dimethyl) phenyl] 2,6-dimethyl benzoquinoneimine | 50 g |

This composition is applied as a rinse to naturally dark blond hair. After drying, the hair is brightened and further exhibits a beautiful pearly glint.

EXAMPLE 43

A hair-setting lotion is prepared by mixing, immediately before application, 0.100 g of a powder $P_{43}$ and 25 cc of a solution $S_{43}$ defined below:

| Powder $P_{43}$: | |
|---|---|
| N-[(4'-hydroxy 2',6'-dimethyl) phenyl] 2,6-dimethyl benzoquinoneimine | 4 g |
| N-[(4'-amino 3'-methyl) phenyl] 2,6-dimethyl benzoquinoneimine | 0.4 g |
| N-[(2',4'-diamino 5'-methyl) phenyl] 2-chloro benzoquinoneimine | 0.4 g |
| Polyvinylpyrrolidone (as in Example 1), q.s.p. | 100 g |
| Solution $S_{43}$: | |
| Polyvinylpyrrolidone (as in Example 1) | 2.0 g |
| Ethyl alcohol | 40 cc |
| Butyl Cellosolve | 2 cc |
| Triethanolamine, q.s.p. | pH 7 |
| Water, q.s.p. | 100 cc |

When applied to freshly bleached hair, this lotion gives the hair a particularly aesthetic platinum shade.

What is claimed is:

1. A process for nonpermanently dyeing human hair by applying a hair dye composition to the hair in an amount effective to color the hair, said process comprising
   1. preparing said hair dye composition immediately before application of the same to the hair by incorporating into an aqueous carrier a dye in powder form, said dye being selected from the group consisting of
      a. a compound having the formula $$Y - Ar_1 - N = Ar_2 = X$$

wherein $Ar_1$ and $Ar_2$ each independently are selected from the group consisting of phenyl and pyridyl, each optionally substituted with a member selected from the group consisting of amino, hydroxy, lower alkoxy, lower alkyl, acetylamino and halogen, Y represents a member selected from the group consisting of hydroxy and

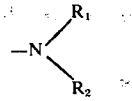

wherein $R_1$ and $R_2$ each independently represents a member selected from the group consisting of hydrogen, lower alkyl and amino lower alkyl wherein the amino moiety is optionally substituted by a member selected from the group consisting of acetyl, carbamyl and mesyl and X represents a member selected from the group consisting of oxygen, imine and iminium group, and
      b. a salt of the compound defined in (a), said composition containing 0.0005–2 percent by weight of said dye, and
   2. applying the thus prepared hair dye composition to the hair in an amount effective to color the hair.
2. The process of claim 1 wherein said aqueous carrier also contains a lower alkanol.
3. The process of claim 2 wherein said lower alkanol is selected from the group consisting of ethanol and isopropanol.
4. The process of claim 1 wherein said aqueous carrier also contains hydrogen peroxide in an amount of about 1–6 percent by weight of said composition.
5. The process of claim 1 wherein said aqueous carrier also contains antioxidizing amounts of butyl hydroxy anisole.

6. The process of claim 1 wherein said aqueous carrier also includes a member selected from the group consisting of butylglycol and benzyl alcohol.

7. The process of claim 1 wherein said composition also includes a direct dye selected from the group consisting of an azo, an anthraquinone, a nitrobenzene and an oxazine dye.

8. The process of claim 1 wherein said composition also includes a cosmetic resin selected from the group consisting of polyvinylpyrrolidone, copolymer of crotonic acid and vinyl acetate, copolymer of vinylpyrrolidone and vinyl acetate and copolymer of maleic anhydride and butyl vinyl ether.

9. The process of claim 1 wherein said composition has a pH of 2.5–10.

10. The process of claim 9 wherein said composition has a pH of 4–10.

11. The process of claim 1 wherein said hair is dried subsequent to the application of said composition thereon without an intermediate washing or rinsing of said hair.

12. The process of claim 1 wherein said hair subsequent to the application of said composition thereon is washed and rinsed prior to drying said hair.

13. In the use of a dye for nonpermanently dyeing human hair with an aqueous hair dye composition containing said dye wherein said aqueous hair dye composition is applied to the hair, the improvement comprising incorporating said dye, in powder form, into an aqueous carrier so as to produce said hair dye composition immediately prior to applying the resulting hair dye composition to the hair, said hair dye being selected from the group consisting of 1. a compound having the formula

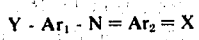

$$Y - Ar_1 - N = Ar_2 = X$$

wherein $Ar_1$ and $Ar_2$ each independently are selected from the group consisting of phenyl and pyridyl, each optionally substituted with a member selected from the group consisting of amino, hydroxy, lower alkoxy, lower alkyl, acetylamino and halogen, Y represents a member selected from the group consisting of hydroxy and

$$-N\begin{matrix}R_1\\R_2\end{matrix}$$

wherein $R_1$ and $R_2$ each independently represents a member selected from the group consisting of hydrogen, lower alkyl and amino lower alkyl wherein the amino moiety is optionally substituted by a member selected from the group consisting of acetyl, carbamyl and mesyl and X represents a member selected from the group consisting of oxygen, imine and iminum group, and 2. a salt of the compound defined in (1), said composition containing 0.0005–2 percent by weight of said dye.

* * * * *